United States Patent [19]

Tsuda

[11] Patent Number: 5,182,201
[45] Date of Patent: Jan. 26, 1993

[54] LIPASE IMMOBILIZATION WITHOUT COVALENT BONDING ON AN AMPHIPHILIC SUPPORT CONTAINING LIPOPHILIC ALKYL CHAINS

[75] Inventor: Yoshihisa Tsuda, Wilmette, Ill.

[73] Assignee: UOP, Des Plaines, Ill.

[21] Appl. No.: 604,038

[22] Filed: Oct. 26, 1990

[51] Int. Cl.$^5$ .................... C12N 11/14; C12N 11/08; C12N 11/06; C12P 7/64
[52] U.S. Cl. .................... 435/176; 435/134; 435/180; 435/181
[58] Field of Search ............... 435/134, 174, 176, 180, 435/181

[56] References Cited

U.S. PATENT DOCUMENTS

| | | | |
|---|---|---|---|
| 3,909,360 | 9/1975 | Horiuchi et al. | 435/178 |
| 4,006,059 | 2/1977 | Butler | 435/179 X |
| 4,141,857 | 2/1979 | Levy et al. | 252/430 |
| 4,267,273 | 5/1981 | Smith | 435/174 X |

Primary Examiner—David M. Naff
Attorney, Agent, or Firm—Thomas K. McBride; Eugene I. Snyder

[57] ABSTRACT

A support matrix particularly suitable for the immobilization of biologically active materials acting on lipophilic substrates results from the reaction of a polyamine-impregnated porous particle with a monofunctional paraffinic aldehyde. The resulting support matrix has a hydrophobic coating providing a microenvironment for the biologically active material, such as an enzyme, and hydrophilic portions for emulsification or binding to polar regions at or near the active site.

33 Claims, No Drawings

LIPASE IMMOBILIZATION WITHOUT COVALENT BONDING ON AN AMPHIPHILIC SUPPORT CONTAINING LIPOPHILIC ALKYL CHAINS

BACKGROUND OF THE INVENTION

Methods for the immobilization of biologically active materials, especially enzymes, have undergone such rapid development in recent years that it is fair to say that support matrices and their preparation are rather mature fields of technology in, for example, enzyme catalyzed reactions of commercial importance. The impetus for their development initially was the conservation of enzymes; the use of enzymes in homogeneous reactions generally mandated the single use of enzymes. Because enzymes often are an expensive component of reactions, and sometimes the most expensive one, there arose the need to develop methods allowing multiple use of enzymes. Immobilization of enzymes on solid supports led to heterogeneous enzyme-catalyzed reactions where the immobilized enzymes could be readily removed, as in a stirred batch reactor, or could be employed in a continuous process, as in a fixed bed, but in either case permitted enzyme-catalyzed processes where the enzyme could be reused until its decreased activity made further use economically unfeasible.

Presently there are a variety of support matrices from which immobilized enzymes specifically, and immobilized biologically active materials generally, can be prepared. Some bind the enzyme, as exemplary of a biologically active material, via ionic interaction, others bind the enzyme via entrapment. In still others the biologically active material is immobilized by covalent bonding to the support or some intermediary linked to the support. Thus, the skilled worker has some realistic alternatives in his technological closet when seeking a support matrix with which to immobilize a biologically active substance.

A type of support matrix which has proved versatile and effective in a wide scope of operations is that described in U.S. Pat. No. 4,141,857. The particles of the matrix are incompressible, hard, unreactive materials, which are desirable properties for good flow characteristics in a packed bed reactor, composed chiefly of porous inorganic oxides coated with an inorganic resin. The latter results from the reaction of a polyamine with a large excess of a bifunctional organic reagent, especially a dialdehyde, to afford a crosslinked polyamine with a multiplicity of pendant aldehyde groups available for covalent bonding to enzymes. However versatile such a support matrix may be, in the course of some investigations we observed limitations which led to an investigation culminating in the present application.

Although enzymes necessarily are active in aqueous media, the substrates on which enzymes act span a large range of hydrophilic character. At one extreme of the spectrum are polyhydroxylic compounds such as sugars, such as glucose, which are highly polar, extremely hydrophilic materials. At or near the other end of the spectrum are triglycerides, especially those of long chain (C12+) fatty acids, where the long hydrocarbon tail of the fatty acids provide a highly hydrophobic environment. (Throughout this application the words "hydrophobic" and "lipophilic" will be used synonymously. Although interchangeable in the context of this application, the terms stress different aspects of the same physical property.) Even though enzymes within a cell are in an aqueous medium, nonetheless the microenvironment of enzymatic reactions is not homogeneous and will in part reflect the hydrophilic-hydrophobic character of the substrate being acted upon. One can expect the microenvironment within which a sugar is enzymatically isomerized will be highly hydrophilic. One also can expect a substantially different microenvironment for the hydrolysis of triglycerides; the long hydrocarbon tail of fatty acids is quite lipophilic, whereas the reaction site of the ester moiety in combination with the reactant water molecule is rather hydrophilic.

A natural consequence of the varying hydrophilic-hydrophobic properties of enzyme substrates is that the particular enzyme acting on a substrate also can be expected to reflect a varying balance of hydrophilic-hydrophobic properties. Although enzymes generally can be expected to be amphiphilic (that is, exhibiting both hydrophilic and hydrophobic properties), nonetheless enzymes acting on hydrophobic substrates can be expected to have more hydrophobic character than enzymes acting on hydrophilic substrates. When an enzyme is removed from its natural environment and immobilized on a support matrix, additional factors must be considered for optimization of the enzyme-mediated reaction in question. In this regard the example of triglyceride hydrolysis is instructive. Triglycerides are water insoluble, and the hydrolytic medium usually is a highly hydrophobic triglyceride phase in which is dispersed a small amount of water. Reaction probably occurs at the oil-water interface, with its attendant discontinuity in hydrophilic-hydrophobic properties. The enzymes catalyzing triglyceride hydrolysis, which collectively are known as lipases, probably have hydrophobic character in most regions, although the active site is likely to be more hydrophilic. At the same time it is desirable that the support matrix have regions of hydrophilicity to accommodate the reactant water molecule and to gain access to the water-oil interface. The result that emerges is that an effective immobilized lipase is one where the support matrix is amphiphilic, with hydrophobic regions for binding the enzyme and hydrophilic regions for binding of water.

The foregoing conceptualization, though useful, has limitations. It appears that, for example, not all lipases are comparably hydrophobic. For some lipases, presumably those with the greatest hydrophobic character, immobilization on a support with hydrophobic properties effectively binds the enzyme without interfering with its expression of enzyme activity and the resulting immobilized enzyme manifests a higher activity than one immobilized on a more hydrophilic support. Other lipases appear to be less hydrophobic, and for these immobilization on a hydrophobic support does not result in any increase of enzymatic activity, although no decrease in activity may be observed relative to the enzyme immobilized on a hydrophilic support.

There is another aspect of lipases in the hydrolysis of fats and oils which my invention addresses. The enzymatic hydrolysis of lipids using a 1,2,3-nonspecific lipase often is slow with complete hydrolysis difficult to achieve. During the hydrolysis, a large amount of diglycerides are accumulated in the reaction mixture because lipases hydrolyze diglycerides slowly compared to the hydrolysis of triglycerides. To avoid the accumulation of diglycerides in the reaction mixture, an excess amount of lipase is used to carry out a successful hydrolysis. The use of an immobilized lipase requires an enzyme support which is able to absorb a large amount of lipase and to express the full catalytic activity of the absorbed enzyme. The support matrix of this invention and the immobilized lipases prepared therefrom are particularly effective in these regards. In addition, the support has both polar and hydrophobic sites so as to behave as an emulsifier between oil and water.

Our invention is a support matrix for the immobilization of biologically active material having both a hydrophobic region for binding biologically active material, especially with substantial hydrophobic character, and a hydrophilic region for binding with one or more components of the reaction medium. Such a support matrix has the advantages of expressing higher activity of lipophilic enzymes, such as lipases, while affording access to hydrophilic sites, especially to the oil-water interface at which an enzyme-catalyzed reaction occurs.

SUMMARY OF THE INVENTION

The purpose of this invention is to prepare a support matrix simultaneously suited for binding a hydrophobic enzyme while having hydrophilic sites available for other reaction components or as an emulsifier. An embodiment comprises a porous inorganic oxide impregnated with a polyamine which is reacted with a monofunctional aldehyde. In a more specific embodiment the porous inorganic oxide is an alumina. In a yet more specific embodiment the aldehyde contains at least 5 carbon atoms. In a still more specific embodiment the polyamine is a polyethyleneimine. Other embodiments and purposes will become apparent from the ensuing description.

DESCRIPTION OF THE INVENTION

We have found that immobilization of enzymes which have substantial hydrophobic character on a support matrix which is amphiphilic often affords an immobilized enzyme system with enhanced expression of enzyme activity. A suitable support matrix is one with a porous inorganic oxide impregnated with a polyamine which is reacted with one or more monofunctional aldehydes, generally in excess. The reaction of the polyamine with the aldehyde converts the initial coating of the polyamine from a hydrophilic one to a hydrophobic coating, while leaving undisturbed those hydrophilic regions of the support which do not arise from the polyamine. It is found that lipophilic (hydrophobic) enzymes readily bind to the hydrophobic coating, and the resulting immobilized enzyme often is more effective than other types of immobilized enzyme systems when acting on a hydrophobic substrate, especially where the reaction occurs at an oil-water interface.

The support matrix of this invention is only superficially related to that described in U.S. Pat. No. 4,141,857. The latter is a porous material, such as an inorganic oxide, impregnated with a polyamine which is subsequently reacted with a large excess of a bifunctional aldehyde. The reaction with excess bifunctional aldehyde effects crosslinking of the polyamine and simultaneously provides a multiplicity of pendant aldehyde groups. The plethora of reactive aldehydic groups dangling from the now crosslinked polyamine immobilizes enzymes by covalent bonding between the pendant aldehyde groups and the primary amino groups of the enzyme. In contrast, although the support matrices of this invention start off similarly as being porous materials impregnated with polyamines, the latter are reacted with monofunctional aldehydes in order to chemically modify the free amino moiety sites, usually as completely as possible. The reaction of the amino moieties with the aldehyde groups both removes a highly polar environment from the coating and also introduces a lipophilic alkyl chain arising from the aldehyde. In combination the coating is transformed from a hydrophilic to a hydrophobic one. It is important to note that our support matrix has no pendant functional (aldehyde) groups, nor does it bind an enzyme via covalent bonding.

The support matrix of our invention is composed essentially of small particles having a durable coating of the reaction product of a polyamine with a monofunctional aldehyde. The particles which are coated need to provide structural integrity, especially mechanical strength, have good characteristics in a system where there is a liquid flow, and provide a surface, wholly or in part, to which a layer of organic material can be attached. Hard, incompressible particles fulfill the first two requirements, and porous particles meet the last requirement. Materials suitable for use in our invention include refractory metal oxides generally, and especially alumina, silica, thoria, magnesia, boria, titania, zirconia, and combinations thereof, and also include porous glass and various ceramics. Alumina is a particularly favored material in the practice of our invention.

The hard, incompressible, porous particle is then impregnated with a polyamine. One class of polyamines which are especially favored in the practice of our invention is the class of poly(ethyleneamines). These materials are exemplified by diethylenetriamine, triethylenetetraamine, tetraethylenepentamine, pentamethylenehexamine, and polyethyleneimine, with the latter being one of the polyamines of choice. The molecular weight of the particular polyethyleneimine used is not especially critical to the success of our invention. Polyethyleneimines having a molecular weight between about 2,000 and about 20,000 are most often utilized in our invention, and those having a molecular weight between about 8,000 and 15,000 are particularly favored. Since the support matrix in many cases may be used for food applications, the use of a food grade polyamine may be mandatory in these applications, as is apparent to the skilled worker. Another class of polyamines which may be used in our invention, although not necessarily with strictly equivalent results, are the terminally disubstituted diaminoalkanes, such as 1,2-diaminoethane (ethylene diamine), 1,3-diaminopropane (propylene diamine), 1,4-diaminobutane, 1,5-diaminopentane, 1,6-diaminohexane, 1,7-diaminoheptane, 1,8-diaminooctane, and so forth. The particles may be impregnated with from about 2 up to about 20 weight percent polyamine, although the range between about 8 and 15 weight percent is the more usual one.

Polyamines generally are used in aqueous solutions containing from about 0.5 to about 10% by weight of polyamine, although the concentration is not in any way critical. Generally the porous support and solution of polyamine are contacted with mixing for a time sufficient to ensure impregnation, which is between about 0.5 to about 3 hours. Excess polyamine is then removed, as by decantation or filtration. The polyamine-impregnated porous support may then be dried prior to further treatment, although drying is not a necessary feature of this invention.

The polyamine of the impregnated support is reacted with a monofunctional aliphatic aldehyde, generally under mildly acidic conditions, i.e., a pH of less than about 0.6. Control of pH may be effected by any acid, although the use of organic carboxylic acids to achieve the desired reaction pH is highly recommended. Among the carboxylic acids formic and acetic acids are by far the most convenient to use. The monofunctional aldehydes which are reacted with the polyamine are saturated paraffinic aldehydes, i.e., those with the formula $C_nH_{2n+1}CHO$. Aldehydes having at least 5 carbon atoms appear to be suitable in providing the desired hydrophobicity to the resulting coating. It can be readily appreciated that the longer the alkyl chain of the aldehyde (that is, the greater the carbon number of the aldehyde) the greater will be the hydrophobicity of the resulting coating. Consequently one has some degree of control over the hydrophobic character of the support matrix by careful choice of the reactant monofunctional aldehyde. Since the hydrophobicity of enzymes itself varies, simply varying the chain length of the aldehyde will tend to tailor the hydrophobicity of the resulting support matrix to that of the enzyme to be immobilized in order to obtain an immobilized enzyme system having optimum enzymatic expression.

Although aldehydes containing from about 5 to about 20 carbon atoms may be used in the practice of this invention, it is most common to employ aldehydes having between about 6 and about 12 carbon atoms, principally because of availability, especially in a food grade, and also because the desired control of hydrophobicity usually can be achieved with this range of aldehydes. In terms of the formula $C_nH_{2n+1}CHO$, n is an integer from about 4 to about 19, but most usually in the range between about 5 and about 11. Examples of suitable aldehydes include pentanal, hexanal, heptanal, octanal, nonanal, decanal, undecanal, dodecanal, tridecanal, tetradecanal, pentadecanal, hexadecanal, heptadecanal, octadecanal, nonadecanal, and eicosanal.

The polyamine-impregnated porous particles are reacted with a solution of the aldehyde in an unreactive organic solvent. By "unreactive" organic solvent is meant one which does not react either with the amine or the aldehyde. Thus, for example, alcohols generally are not favored as organic solvents because they can too easily form acetals with the aldehydes. The concentration of the aldehyde in the organic solvent is not important to the success of this invention, and it has been found that a concentration between about 1 and 5 weight percent aldehyde in solvent is quite satisfactory. As previously mentioned, reaction best occurs under acidic conditions, and the aldehyde solution generally will contain an organic carboxylic acid, such as formic or acetic acids, at a concentration between about 0.5 and 3 weight percent, although the acid concentration also is not particularly important to the success of our invention.

The occurrence of a reaction is readily seen by the formation of a yellow color under reaction conditions. Reaction occurs under a very wide range of conditions including a temperature between ambient and about 100° C. for a time ranging from several minutes to several hours. As a benchmark, reactions conducted at 60° C. generally are complete within about 30 minutes. The amount of aldehyde used most often is in the range from about 10 to about 500 weight percent based on the polyamine, depending upon the molecular weight of the polyamine and its amine content, as well as the molecular weight of the monofunctional aldehyde employed, and the degree of reaction of the free amino groups sought. Larger amounts of aldehyde may be used, though ordinarily it will be without incremental effect. After the polyamine and monofunctional aldehyde have reacted, the resulting material is washed well with an organic solvent, usually the one employed in the reaction mixture, to remove unreacted aldehyde. The resulting material is then optionally dried to afford the support matrix which may be stored prior to use.

The biologically active materials which may be immobilized on the support matrix of our invention include enzymes, cofactors, antibodies, antigens, and other proteinaceous materials, especially those which have appreciable lipophilic character. The lipases as a group are exemplary of enzymes which act on largely lipophilic substrates, and may in fact be the most important class of enzymes which are advantageously immobilized on the support matrix described above. Although the support matrix of this invention may be most advantageously used with hydrophobic enzymes and other hydrophobic biologically active materials, it needs to be stressed that hydrophobic character is not a requirement for the biologically active material to be immobilized on the support matrix of this invention.

Immobilization of biologically active materials on the support matrix of this invention is usually a simple process involving little, if at all, more than contacting or agitating an aqueous solution of the biologically active material under immobilizing conditions. Using an enzyme as illustrative, an aqueous solution of the enzyme may be contacted with the support matrix at a temperature from about 1° to about 60° C., at a pH normally near 7, and for a time effective to ensure immobilization of the material under the conditions used. What is important is that the conditions used for immobilization not significantly alter the activity of the biologically active material, consequently low temperatures (1° to 25° C.) normally are used. In any event, immobilization of such materials as enzymes are sufficiently known to the skilled person that no further elaboration is needed.

The following examples are merely illustrative of our invention and not intended to limit it in any way.

EXAMPLE 1

General Procedures

Preparation of support matrix.

Gamma-alumina, 35/50 mesh, was impregnated with poly(ethyleneimine) by thoroughly mixing the alumina with an aqueous solution of poly(ethyleneimine) followed by slow evaporation of the water under gentle heating. The aqueous solutions generally were on the order of 10 weight percent polyamine, and sufficient solution was used to afford a finished product containing 10–13 weight percent poly(ethyleneimine).

The polyamine-impregnated supports were reacted with aldehydes according to the following general procedure. Ten grams of polyamine-impregnated support was added to 100 mL of acetone solution containing 1% formic acid and 2 weight percent of a monofunctional aldehyde. The suspension was heated at 60° C. for 30 minutes with occasional shaking, after which solid was removed by filtration through a Buchner funnel. The solid was washed with 100 mL of acetone, then air dried at room temperature overnight to afford the finished support matrix.

Immobilized lipase was prepared by mixing appropriate amounts of an aqueous lipase solution with the support for about 30 minutes at room temperature. The solid was collected by filtration, washed with water, and then air dried overnight.

Determination of lipase activity: assay.

The activity of the immobilized lipase preparations was determined according to the following assay procedure. To a mixture of 8 g olive oil and 8 g citrate buffer (0.2M) at pH 6.0 was added 0.5 g dried lipase sample (water content ca. 3–8%). The mixture was shaken (120 oscillations per minute) for one hour at 50° C., after which the mixture was centrifuged and the oil layer was analyzed by high pressure liquid chromatography for triglycerides, diglycerides, and free fatty acids using a C-18 column with a mobile phase of 70:30 acetone:acetonitrile. Triglyceride hydrolysis was the difference between triglyceride concentration at time zero and triglyceride concentration at the end of assay time.

EXAMPLE 2

Effect of aldehyde chain length on immobilization of lipase.

The preparation of supports resulting from the use of diverse aldehydes was performed according to the general procedure in Example 1. To 5 grams of the finished support were added a solution containing 33,400 units of a yeast lipase (Amano, Lipase AY-30). After 30 minutes at room temperature, the immobilized lipase was washed with water and dried, and its catalytic activity was determined at 50° C. Results are summarized in the following Table 1. The results show that, at least with this particular lipase, activity decreases with increasing chain length and is at a maximum with short chain aldehyde.

TABLE 1

Effect of Chain Length of Aldehyde on Immobilization of Lipase

| Aldehyde | Amt of Aldehyde,[a] gram | % Fatty Acid[b] Formation | % Diglyceride[b] Formation | % Triglyceride[b] Hydrolysis |
| --- | --- | --- | --- | --- |
| Hexanal | 0.2 | 35.6 | 13.0 | 58.0 |
| Octanal | 0.2 | 34.4 | 13.4 | 57.3 |
| Decanal | 0.2 | 33.2 | 14.0 | 54.0 |
| Dodecanal | 0.2 | 30.8 | 14.3 | 51.9 |

[a]Grams aldehyde reacted per gram PEI-impregnated alumina.
[b]Assays were performed using 0.5 g immobilized lipase (AY-30; see Example 4) at 50° C., 1 hour reaction time, using the general procedure described in Example 1.

EXAMPLE 3

Effect of aldehyde concentration on immobilization of lipase.

In this experiment there was examined the influence of the amount of octanal added to prepare the support matrix. To the finished support matrix was added an aqueous solution of lipase containing 33,400 units per 5 grams of support, and the immobilized enzyme system was prepared as described in the prior example. The results, summarized in Table 2, show a definite increase in activity with the amount of aldehyde used in the reaction mixture.

TABLE 2

Effect of Octanal Concentration on the Immobilization of Lipase[a]

| Amt of Octanal[b], gm | % Fatty Acid[c] Formation | % Diglyceride[c] Formation | % Triglyceride[c] Hydrolysis |
| --- | --- | --- | --- |
| 0.10 | 29.2 | 13.0 | 54.4 |
| 0.15 | 31.2 | 12.6 | 55.7 |
| 0.20 | 32.6 | 12.0 | 57.1 |
| 0.25 | 35.6 | 11.9 | 60.6 |

[a]Lipase used in amount of 6,680 units/gram support matrix.
[b]Grams octanal per gram PEI-impregnated alumina.
[b]Assays were performed using 0.5 g immobilized lipase (AY-30) at 50° C., 1 hour reaction time, using the general procedure described in Example 1.

EXAMPLE 4

Activities of various immobilized lipases.

The activity of various immobilized lipases was determined using a support matrix where the polyamine was polyethyleneimine and the aldehyde was octanal in the amount of 2 grams aldehyde per 10 gram of polyamines PEI-impregnated alumina. Comparisons also were done using as a support matrix a lecithin coated alumina and a support matrix where the polyethyleneimine was reacted with hexanal. Lipases absorbed on polyethyleneimine-impregnated alumina expressed virtually no activity. The various lipases used were obtained from Amano International Enzyme Co. and included a bacterial lipase, P-30, from *Pseudomonas sp.*, a mold lipase, AP, from *Aspergillus niger*, and a yeast lipase, AY-30, from *Candida Cylindracea*. The reaction mixture contained 8 grams of olive oil and 8 grams of a citrate buffer (0.2M), pH 6.0 per gram of immobilized lipase. The mixture was incubated at 50° C. for either 3 or 5 hours as indicated. The product was separated by centrifugation and triglycerides and diglycerides were measured by high pressure liquid chromatography. As the results in Table 3 clearly indicate, the nature of the support matrix can have substantial and important effects on the activity of the lipase. Comparison of the last two entries also shows the importance of the aldehyde used in the preparation of the support matrix, at least for some lipases.

TABLE 3

Activities of Immobilized Lipase on Various Support Matrices

| Lipase Immobilized | Specificity of Lipase | Supports Used for Immob. | Units of Lipase per gram of Supports | LIPASE ASSAY[b] | |
| --- | --- | --- | --- | --- | --- |
| | | | | Hours | % Triglyceride Hydrolysis | % Diglyceride Formation |
| P-30 | 1, 2, 3 | Lecithin[a] | 10,600 | 5 | 82.5 | 18.4 |
| AY-30 | 1, 2, 3 | Lecithin[a] | 10,020 | 5 | 83.8 | 10.3 |
| AY-30 | 1, 2, 3 | Lecithin[a] | 6,680 | 5 | 72.4 | 16.4 |
| AY-30 | 1, 2, 3 | PEI-OCTANAL | 10,020 | 3 | 96.3 | 3.3 |
| AY-30 | 1, 2, 3 | PEI-OCTANAL | 6,680 | 3 | 96.9 | 2.7 |
| AP | 1, 3 | Lecithin[a] | 32,800 | 5 | 51.1 | 20.3 |

TABLE 3-continued

Activities of Immobilized Lipase on Various Support Matrices

| Lipase Immobilized | Specificity of Lipase | Supports Used for Immob. | Units of Lipase per gram of Supports | LIPASE ASSAY[b] | | |
|---|---|---|---|---|---|---|
| | | | | Hours | % Triglyceride Hydrolysis | % Diglyceride Formation |
| AP | 1, 3 | PEI-OCTANAL | 32,800 | 5 | 67.6 | 20.8 |
| AP | 1, 3 | PEI-OCTANAL | 32,800 | 3 | 55.7 | 20.6 |
| AP | 1, 3 | PEI-HEXANAL | 32,800 | 3 | 16.1 | 9.6 |

[a]Lecithin-coated gamma-alumina
[b]Assays performed using 1.0 g of immobilized lipase at 50° C.

What is claimed is:

1. A method of making an amphiphilic support matrix for the immobilization of lipophilic biologically active materials without covalent bonding comprising impregnating a hard, incompressible porous particle with a hydrophilic polyamine, to provide a coating of hydrophilic polyamine on the particle reacting the hydrophilic polyamine coating with a monofunctional, saturated aliphatic aldehyde containing a lipophilic alkyl chain of at least 5 carbon atoms, to convert the hydrophilic polyamine coating to a hydrophobic coating while retaining hydrophilic sites to produce an amphiphilic support matrix removing unreacted aldehyde, and recovering the resulting amphiphilic support matrix.

2. The method of claim 1 where the particle is selected from the group consisting of refractory metal oxides, glass, and ceramics.

3. The method of claim 2 where the particle is a refractory metal oxide selected from the group consisting of alumina, silica, thoria, boria, magnesia, titania, zirconia, and combinations thereof.

4. The method of claim 3 where the particle is alumina.

5. The method of claim 1 where the polyamine is selected from the group consisting of poly(ethyleneamines) and terminally disubstituted diaminoalkanes.

6. The method of claim 5 where the polyamine is polyethyleneimine.

7. The method of claim 1 where the aldehyde is a paraffinic aldehyde containing from 5 to about 20 carbon atoms.

8. The method of claim 7 where the paraffinic aldehyde contains from 6 to about 12 carbon atoms.

9. The method of claim 1 where the polyamine and aldehyde are reacted at a pH less than about 6.

10. The method of claim 9 where the polyamine and aldehyde are reacted at a pH less than about 6 using an organic carboxylic acid to achieve the pH of less than about 6.

11. The method of claim 10 where the organic carboxylic acid is formic or acetic acid.

12. A support matrix for the immobilization of lipophilic biologically active material resulting from the process of claim 1.

13. The support matrix of claim 12 where the particle is selected from the group consisting of refractory metal oxides, glass, and ceramics.

14. The support matrix of claim 13 where the particle is a refractory metal oxide selected from the group consisting of alumina, silica, thoria, boria, magnesia, titania, zirconia, and combinations thereof.

15. The support matrix of claim 14 where the particle is alumina.

16. The support matrix of claim 12 where the polyamine is selected from the group consisting of poly(ethyleneamines) and terminally disubstituted diaminoalkanes.

17. The support matrix of claim 16 where the polyamine is polyethyleneimine.

18. The support matrix of claim 12 where the aldehyde is a paraffinic aldehyde containing from 5 to about 20 carbon atoms.

19. The support matrix of claim 18 where the paraffinic aldehyde contains from 6 to about 12 carbon atoms.

20. The support matrix of claim 12 where the polyamine and aldehyde are reacted at a pH less than about 6.

21. The support matrix of claim 20 where the polyamine and aldehyde are reacted at a pH less than about 6 using an organic carboxylic acid to achieve the pH of less than about 6.

22. The support matrix of claim 12 where the organic carboxylic acid is formic or acetic acid.

23. A method of making an immobilized lipase comprising impregnating a hard, incompressible porous particle with a hydrophilic polyamine to provide a coating of hydrophilic polyamine on the particle, reacting the hydrophilic polyamine coating with a monofunctional, saturated aliphatic aldehyde containing a lipophilic alkyl chain of at least 5 carbon atoms to convert the hydrophilic polyamine coating to a hydrophobic coating while retaining hydrophilic sites to produce an amphiphilic support matrix; removing unreacted aldehyde, contacting the resulting amphiphilic support matrix with an aqueous solution of a lipase under immobilizing conditions for a time effective to immobilize the lipase thereon without covalent bonding, and recovering the resulting immobilized lipase.

24. The method of claim 23 where the particle is selected from the group consisting of refractory metal oxides, glass, and ceramics.

25. The method of claim 24 where the particle is a refractory metal oxide selected from the group consisting of alumina, silica, thoria, boria, magnesia, titania, zirconia, and combinations thereof.

26. The method of claim 25 where the particle is alumina.

27. The method of claim 23 where the polyamine is selected from the group consisting of poly(ethyleneamines) and terminally disubstituted diaminoalkanes.

28. The method of claim 27 where the polyamine is polyethyleneimine.

29. The method of claim 23 where the aldehyde is a paraffinic aldehyde containing from 5 to about 20 carbon atoms.

30. The method of claim 29 where the paraffinic aldehyde contains from 6 to about 12 carbon atoms.

31. The method of claim 23 where the polyamine and aldehyde are reacted at a pH less than about 6.

32. The method of claim 31 where the polyamine and aldehyde are reacted at a pH less than about 6 using an organic carboxylic acid to achieve the pH of less than about 6.

33. The method of claim 32 where the organic carboxylic acid is formic or acetic acid.

* * * * *